US012806302B2

(12) United States Patent
Cromartie

(10) Patent No.: US 12,806,302 B2
(45) Date of Patent: Nov. 24, 2026

(54) SANITIZING APPARATUS

(71) Applicant: Cro Invention LLC, Mableton, GA (US)

(72) Inventor: Robert Cromartie, Mableton, GA (US)

(73) Assignee: Cro Invention LLC, Mableton, GA (US)

( * ) Notice: Subject to any disclaimer, the term of this patent is extended or adjusted under 35 U.S.C. 154(b) by 691 days.

(21) Appl. No.: 18/307,248

(22) Filed: Apr. 26, 2023

(65) Prior Publication Data

US 2023/0338600 A1 Oct. 26, 2023

Related U.S. Application Data

(60) Provisional application No. 63/335,136, filed on Apr. 26, 2022.

(51) Int. Cl.
*A61L 2/26* (2006.01)
*A61L 2/18* (2026.01)

(52) U.S. Cl.
CPC .. *A61L 2/26* (2013.01); *A61L 2/18* (2013.01)

(58) Field of Classification Search
CPC ..................................... A61L 2/26; A61L 2/18
See application file for complete search history.

(56) References Cited

U.S. PATENT DOCUMENTS

2023/0248872 A1* 8/2023 Tajong ...................... A61L 2/18
422/292

* cited by examiner

*Primary Examiner* — Sean E Conley
(74) *Attorney, Agent, or Firm* — BEKIARES ELIEZER LLP

(57) ABSTRACT

The present disclosure provides a sanitizing apparatus comprising: a handle portion comprising: an outer housing configured to be grasped by a hand of a user, an inner housing defining a cavity, and a rim extending inward from the inner housing, the rim configured to define a predetermined area for housing a portion of a cleaning portion; and the cleaning portion fixedly secured to the handle portion within the predetermined area defined by the rim, the cleaning portion comprising: a structural core, at least a portion of the structural core being housed in the handle portion, and a pliable disinfecting portion fixed around the structural core, wherein at least a portion of the pliable disinfecting portion is disposed in the predetermined area defined by the rim.

20 Claims, 8 Drawing Sheets

100

*FIG. 6*
Easy to carry in pockets or purses.
Easy to use and dispose.
Flexible wand that swipes a surface easily.
Mess FREE because your hands never touch the dirty surface!
Perfect for:
Work • School • Travel • Camping
INGREDIENTS
WATER, GLYCERIN, MUGWORT, LEMONGRASS, LAVENDER, ORANGE BLOSSOM, BENZALKONIUM CHLORIDE, POLYHEXAM-ETHYLENE GUANIDINE (PHMG), FRAGRANCE, COLOUR.
DISINFECTANT: ALCOHOL- FREE SANITIZER
MATERIAL: POLYPROPYLENE (PP)
6.3 IN

100

SANITIZING APPARATUS

RELATED APPLICATION

Under provisions of 35 U.S.C. § 119(e), the Applicant claims benefit of U.S. Provisional Application No. 63/335,136 filed on Apr. 26, 2022, and having inventors in common, which is incorporated herein by reference in its entirety.

It is intended that the referenced application may be applicable to the concepts and embodiments disclosed herein, even if such concepts and embodiments are disclosed in the referenced application with different limitations and configurations and described using different examples and terminology.

FIELD OF DISCLOSURE

The present disclosure generally relates to devices configured for disinfecting and sanitizing surfaces.

BACKGROUND

The desire to disinfect and/or sanitize surfaces is commonplace when coming in contact with surfaces in public spaces and/or utilities. For example, a toilet of a public restroom may have unwanted residue and/or any number of easily transmissible microbes, bacteria, and/or viruses residing on the surface of the toilet seat. The conventional means of avoiding undesired contact with said surfaces are the use of toilet paper to cover the seat, a disposable sanitary wipe, or if lucky, an available disposable toilet seat cover. This often causes problems because the conventional means fall short in a number of ways.

First, the unwanted disposable sanitary wipes require hand contact, albeit through the wipe, of one's hand directly to the toilet seat. Said wipe may be insufficient size to fully sanitize and the wipe may rip in any number of ways. Second, toilet paper and/or a toilet seat cover do not kill any of the mentioned unwanted organisms, easily rip, and can easily deform if any adjustment and/or perspiration occurs.

A user-friendly device that disinfects while preventing unwanted contact with a surface is desired.

BRIEF OVERVIEW

This brief overview is provided to introduce a selection of concepts in a simplified form that are further described below in the Detailed Description. This brief overview is not intended to identify key features or essential features of the claimed subject matter. Nor is this brief overview intended to be used to limit the claimed subject matter's scope.

In one aspect, the present disclosure may provide a sanitizing apparatus comprising: a handle portion comprising: an outer housing configured to be grasped by a hand of a user, an inner housing defining a cavity, and a rim extending inward from the inner housing, the rim configured to define a predetermined area for housing a portion of a cleaning portion; and the cleaning portion fixedly secured to the handle portion within the predetermined area defined by the rim, the cleaning portion comprising: a structural core, at least a portion of the structural core being housed in the handle portion, and a pliable disinfecting portion fixed around the structural core, wherein at least a portion of the pliable disinfecting portion is disposed in the predetermined area defined by the rim.

In another aspect, the present disclosure may provide a sanitizing apparatus comprising: a handle portion; a disinfecting portion being substantially cylindrical in shape and comprising: a disinfecting portion aperture, and a plurality of divots disposed proximate to an end of the disinfecting portion, each of the plurality of divots being configured to receive a flange, of a plurality of flanges, within the handle portion; and a disinfecting base housed in the disinfecting portion aperture and protruding from the disinfecting portion, the protruding portion of the disinfecting base being secured within the handle portion.

In another aspect, the present disclosure may provide a sanitizing apparatus comprising: a handle portion comprising: an outer housing, and an inner housing defining an aperture, a core secured to the inner housing by the aperture receiving the core, wherein at least a portion of core protrudes from the handle portion; and a cleaning applicator secured to the protruding portion of the core, at least a portion of the cleaning applicator being housed in the aperture and secured within the aperture via one or more flanges inserted into one or more divots defined in the cleaning applicator.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicant. In addition, the drawings may contain other marks owned by third parties and are being used for illustrative purposes only. All rights to various trademarks and copyrights represented herein, except those belonging to their respective owners, are vested in and the property of the Applicant. The Applicant retains and reserves all rights in its trademarks and copyrights included herein, and grants permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure. In the drawings.

DETAILED DESCRIPTION

Figure 1:
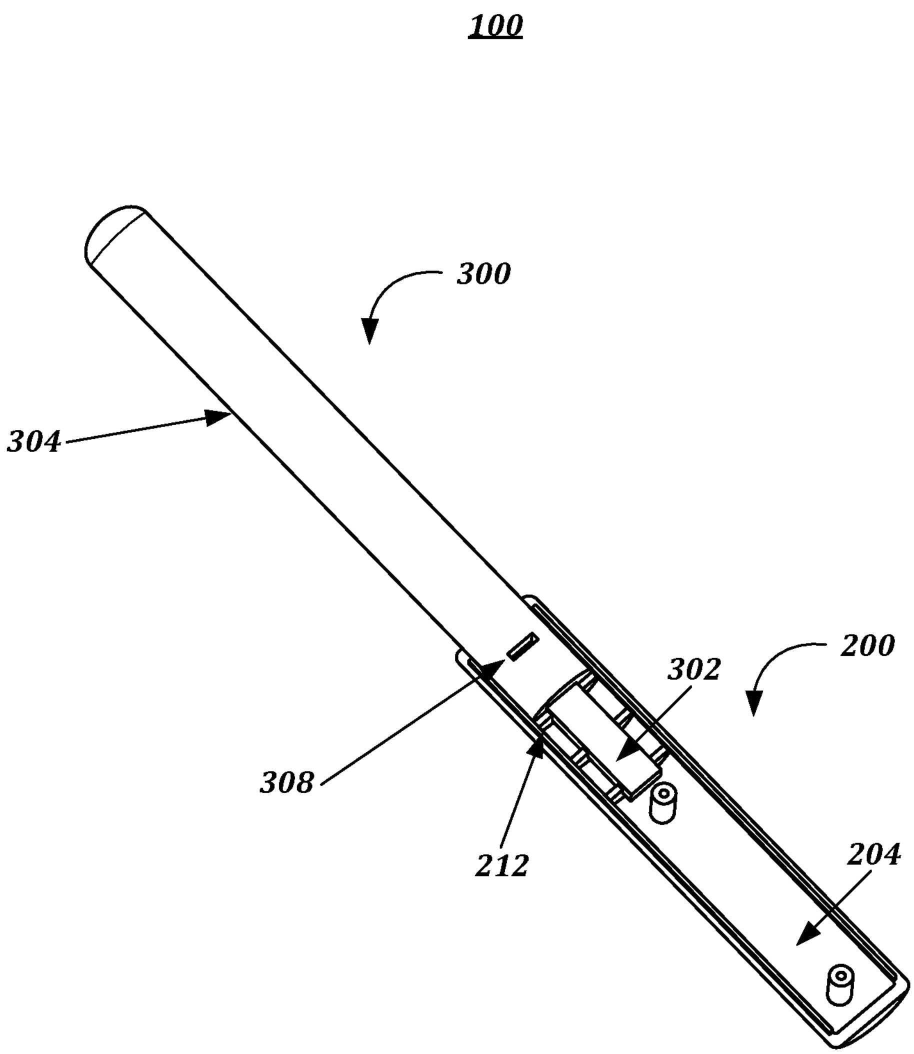
FIG. 1 illustrates a sanitizing apparatus 100 with half of a handle portion 200 removed.
Figure 2:
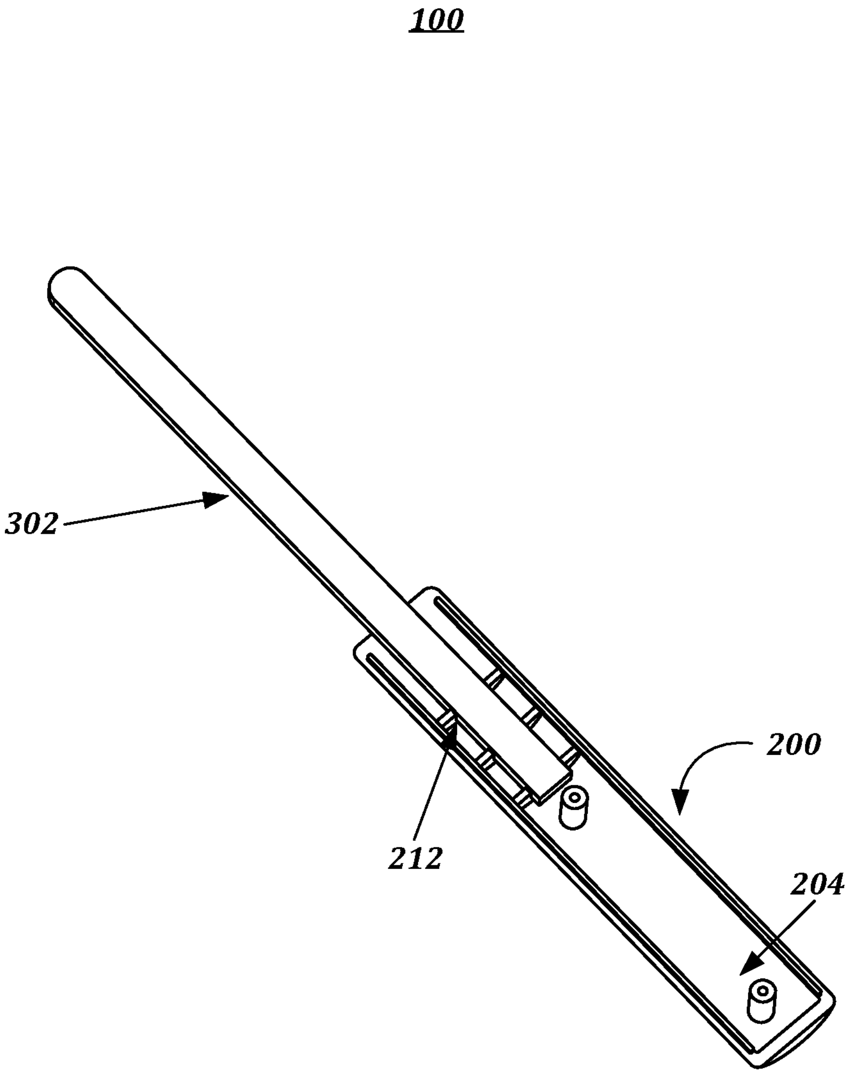
FIG. 2 illustrates a portion of the handle portion 200 and a core 302.
Figure 3:
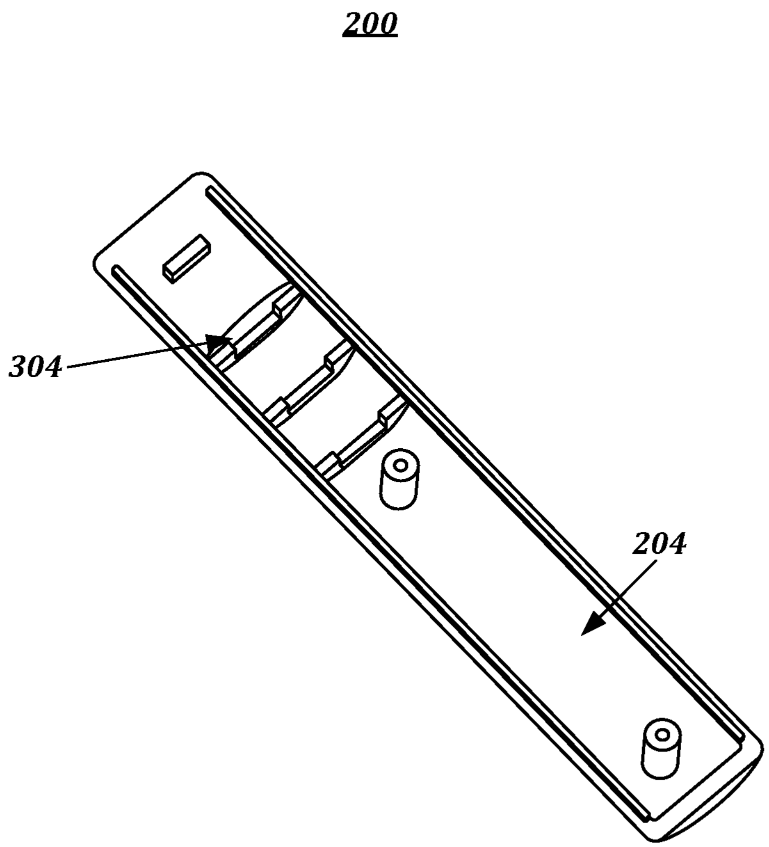
FIG. 3 illustrates a portion of the handle portion 200.
Figure 4C:
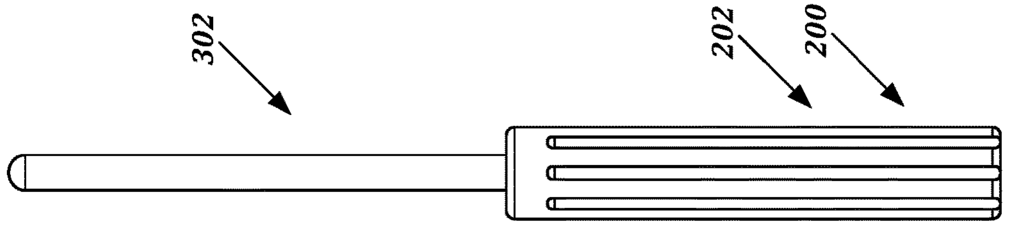
FIG. 4C illustrates the core 302 and the handle 200.
Figure 4B:
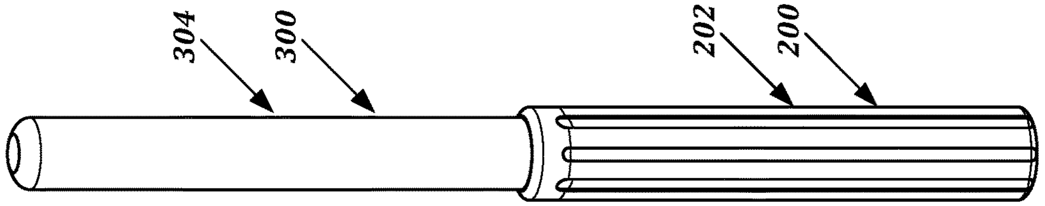
FIG. 4B illustrates a perspective view of the sanitizing apparatus 100.
Figure 4A:
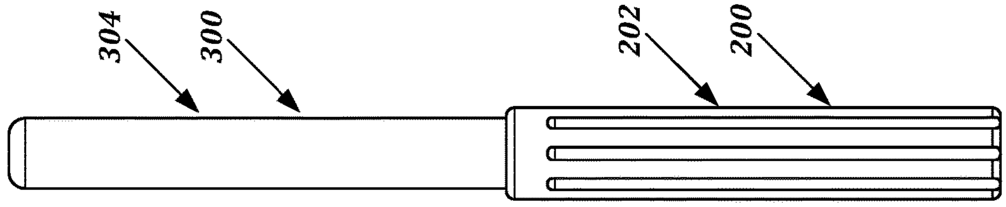
FIG. 4A illustrates a front view the sanitizing apparatus 100.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings.

Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of devices configured for sanitizing and disinfecting surfaces, embodiments of the present disclosure are not limited to use only in this context.

I. APPARATUS OVERVIEW

This overview is provided to introduce a selection of concepts in a simplified form that are further described below. This overview is not intended to identify key features or essential features of the claimed subject matter. Nor is this overview intended to be used to limit the claimed subject matter's scope.

The current device (sanitizing apparatus) may be used for cleaning surfaces. A nonlimiting example of a surface is a toilet seat. The device may have three parts, a handle, a stem connected to the handle, and a cleaning portion secured to the stem. The stem may be used as a structural element, for the cleaning portion. The cleaning portion may be a sponge-like material containing disinfecting properties and/or housing the disinfecting substance. The cleaning portion may further be the portion of the device that contacts the surface for disinfecting. In some aspects, the device may be secured in a wrapper and/or housing element meant to preserve the disinfecting properties until desired use.

Embodiments of the present disclosure may comprise methods, systems, and components comprising, but not limited to, at least one of the following:

A. A Handle Portion 200;

B. A Cleaning Portion 300; and

In some embodiments, the present disclosure may provide an additional set of components for further facilitating the system. The additional set of components may comprise, but not be limited to:

C. A Protective Casing 400.

Details with regards to each component is provided below. Although components are disclosed with specific functionality, it should be understood that functionality may be shared between components, with some functions split between components, while other functions duplicated by the components. Furthermore, the name of the component should not be construed as limiting upon the functionality of the component. Moreover, each stage disclosed within each component can be considered independently without the context of the other stages within the same component or different components. Each stage may contain language defined in other portions of this specifications. Each stage disclosed for one component may be mixed with the operational stages of another component. In the present disclosure, each stage can be claimed on its own and/or interchangeably with other stages of other components.

The following depicts an example of a method of a plurality of methods that may be performed by at least one of the aforementioned components. Various hardware components may be used at the various stages of operations disclosed with reference to each component. For example, although methods may be described to be performed by a single apparatus, it should be understood that, in some embodiments, different operations may be performed by different apparatuses in operating in conjunction with each other. For example, the sanitizing apparatus may be employed in the performance of some or all of the stages disclosed with regard to the methods. Similarly, one apparatus may be employed in the performance of some or all of the stages of the methods. As such, the apparatus may comprise at least one of the architectural components disclosed herein.

Furthermore, although the stages of the following example method are disclosed in a particular order, it should be understood that the order is disclosed for illustrative purposes only. Stages may be combined, separated, reordered, and various intermediary stages may exist. Accordingly, it should be understood that the various stages, in various embodiments, may be performed in arrangements that differ from the ones claimed below. Moreover, various stages may be added or removed without altering or deterring from the fundamental scope of the depicted methods and systems disclosed herein.

Consistent with embodiments of the present disclosure, a method may be performed by at least one of the aforementioned components. The method may comprise the following stages:

- providing a handle portion, the handle portion comprising:
  - an internal housing, and
  - an external housing;
- securing a distal end of a cleaning core to the internal housing of the handle portion, at least a portion of the cleaning core being made from a rigid material;
- securing a cleaning applicator to the cleaning core via securing the cleaning core into an aperture of the cleaning applicator, at least a portion of the disinfecting portion being housed in the inner housing of the handle portion; and
- securing the sanitizing apparatus in a protective casing, the casing being configured to preserve the disinfecting properties of the sanitizing apparatus until use of the sanitizing apparatus is desired.

Both the foregoing overview and the following detailed description provide examples and are explanatory only. Accordingly, the foregoing overview and the following detailed description should not be considered to be restrictive. Further, features or variations may be provided in addition to those set forth herein. For example, embodiments may be directed to various feature combinations and sub-combinations described in the detailed description.

II. SYSTEM CONFIGURATION

One possible embodiment of a component of the apparatus may be provided by the products and services provided by Cro Invention LLC.

Accordingly, embodiments of the present disclosure provide a sanitizing apparatus including, but not limited to:

A. Handle Portion 200

At least FIGS. 1-5 illustrate the handle portion 200 consistent with an embodiment of the disclosure. The handle portion 200 may be referred to interchangeably as, but not limited to, a base portion.

In some embodiments, the handle portion 200 may be configured to be held by a hand of a user of the sanitizing apparatus 100. In some embodiments, the handle portion 200 may be dimensioned ergonomically for use via a hand of a user.

In further embodiments, the handle portion 200 may comprise an outer housing 202. The outer housing 202 may be configured to contact and/or be held by a hand of a user of the sanitizing apparatus 100.

In further embodiments, the handle portion 200 may comprise an inner housing 204. The inner housing 204 may be used to house, connect, and/or secure at least a portion of the cleaning portion 300. The inner housing 204 may define a cavity (and/or aperture) 206. The cavity 206 may be used to receive and/or retain at least a portion of the cleaning portion 300. In some embodiments, the inner housing 204 may comprise one or more flanges 208. At least a portion of the one or more flanges 208 may protrude in an inward direction into the cavity 206. At least a portion of the one or more flanges 208 may be used to secure a portion of the cleaning portion 300. In some embodiments, the inner housing 204 may comprise one or more inner rims 210. At least a portion of the one or more inner rims 207 may be used as a means to prevent inward longitudinal movement of the cleaning portion 300 into the cavity 206. Put another way, at least a portion of the one or more inner rims 207 may be used to define a predetermined area within the cavity to house portions of the cleaning portion 300.

The handle portion 200 may further comprise one or more grooves (and/or indentations) 212. The one or more grooves 212 may be used to increase friction, traction, and/or grip strength of the hand of the user while using the sanitizing apparatus 100. The one or more grooves 212 may span at least a portion of the length of the outer housing 202. In other embodiments the one or more grooves 208 may substantially span the length of the handle portion 200.

At least a portion of the handle portion 200 may be made from, but not limited to, one or more of the following materials:

a. a thermosetting polymer,
b. a thermoplastic urethane (TPU),
c. a thermoplastic elastomer (TPE),
d. polyurethane,
e. a fibrous material,
f. a rigid material,
g. a semirigid material,
h. any type of metal and/or metal alloy, and
i. any other suitable material.

B. Cleaning Portion 300

At least FIGS. 1-5 illustrate the cleaning portion 300 consistent with an embodiment of the disclosure. The cleaning portion 300 may be referred to interchangeably as, but not limited to, a disinfecting portion, a sanitizing portion, and/or a surface contacting portion.

In some embodiments, the cleaning portion 300 may comprise a core 302. The core 302 may be referred interchangeably as, but not limited to, a structural core, a stem, a tongue, an inner portion, a rigid portion, a connecting portion, a disinfecting base, and/or a base core portion. The core 302 may be used to provide structural support to a disinfecting portion 304. The core may be further used to connect the cleaning portion 300 to the handle portion 200.

The core 302 may provide structural integrity for the cleaning portion 300. The core 302 may be made from any of the materials which may be used to form the handle portion 200. In some embodiments, the handle portion 200 and the core 302 may be formed from the same material. In other embodiments, the core 302 may be formed from a different material than the handle portion 200. In some embodiments, a distal end of the core 302 and/or at least a portion of the core 302 may be housed in and/or secured to the handle portion 200, the inner housing 204 of the handle portion 200, and/or the cavity 206 of the handle portion 200 (when the apparatus 100 is in an assembled state).

In some embodiments, the cleaning portion 300 may comprise the disinfecting portion 304. The disinfecting portion 304 may be used to clean one or more surfaces via contacting the one or more surfaces with the disinfecting portion 304. The disinfecting portion 304 may be referred to interchangeably as, but not limited to, an applicator, a cleaning applicator, a disinfecting applicator, and/or a sponge.

Figure 6:
FIG. 6 illustrates a nonlimiting ingredient list of the disinfecting solution for the sanitizing apparatus 100.
Figure 7:
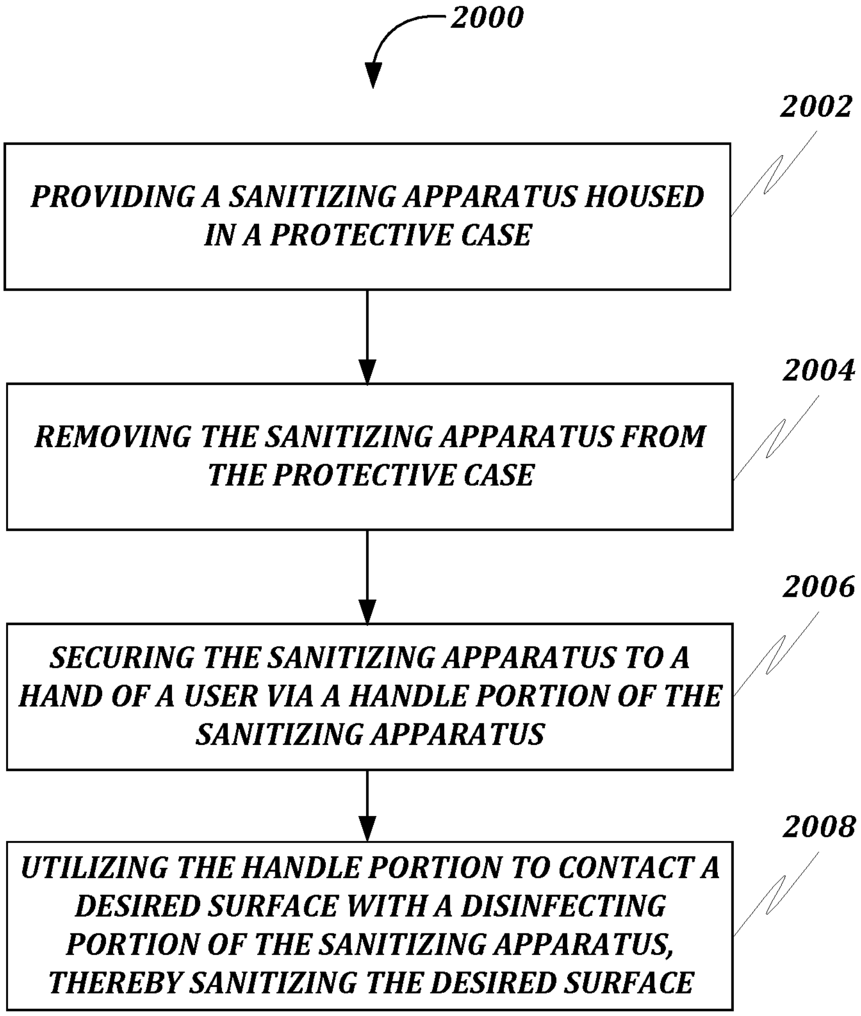
FIG. 7 illustrates a method 2000 for method for sanitizing a desired surface with the sanitizing apparatus.
Figure 8:
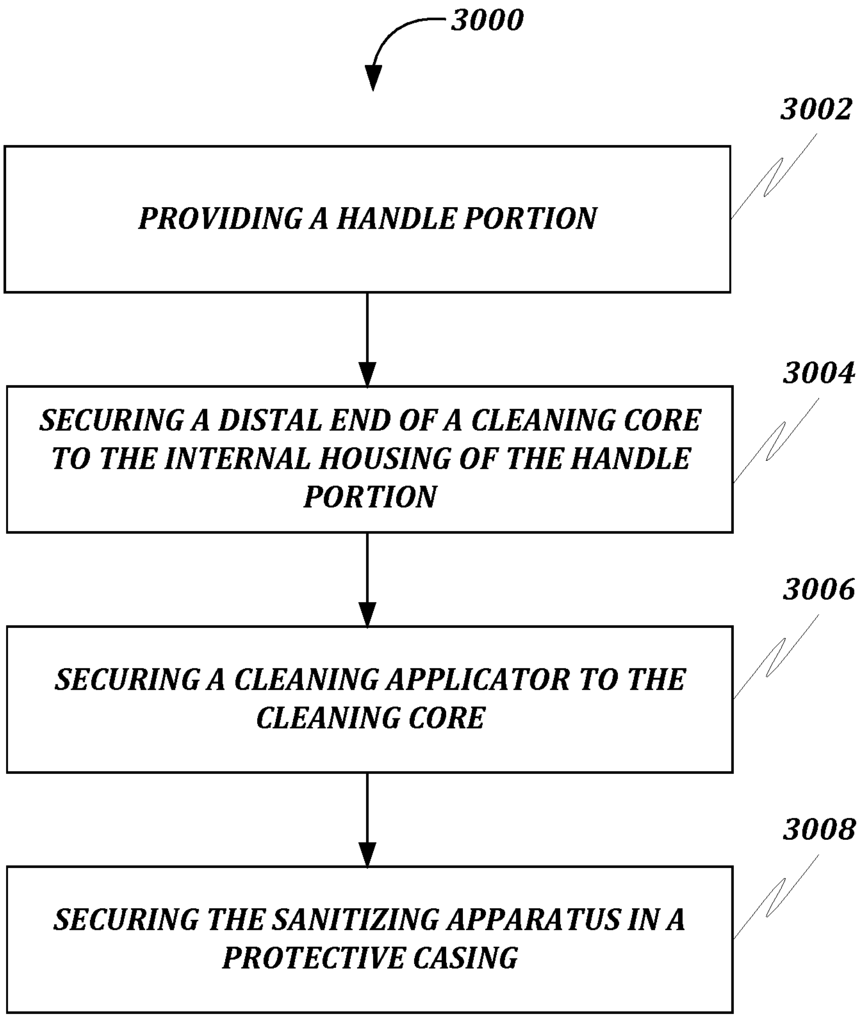
FIG. 8 illustrates a method 3000 for assembling the sanitizing apparatus.

In some embodiments, at least a portion of the disinfecting portion 304 may be made from a pliable, flexible, malleable, absorbent, adsorbent, and/or sponge-like material. In further embodiments, at least a portion of the disinfecting portion 304 may be made from a substantially porous material. In embodiments, at least a portion of the disinfecting portion 304 may be made from any of the aforementioned materials such as, but not limited to, the materials the handle portion may be made from. In further embodiments, illustrated at least in FIG. 6, at least a portion of the disinfecting portion 304 may comprise, be made with, have absorbed therein, have adsorbed thereon, and/or be integrated with, one or more of the following:

a. water,
b. a water solution,
c. mugwort (boosts energy, calms nerves, supports digestion, relieves itching and pain, when absorbed through skin and/or body),
d. lemongrass (natural disinfectant and antioxidant when absorbed through skin and/or body),
e. lavender (fragrance, antifungal, anti-inflammatory, and/or calming effect when absorbed through skin and/or body),
f. orange blossom (fragrance and/or anti-inflammatory when absorbed through skin and/or body),
g. benzalkonium chloride (disinfectant and/or preservative),
h. polyhexamethylene guanidine (PHMG) (guanidine derivative used as a biocidal disinfectant and antifungal),
i. any suitable fragrance,
j. any suitable color additive,
k. any suitable essential oil,
l. an antibacterial substance (and/or agent),
m. an antiseptic substance (and/or agent),
n. an antimicrobial substance (and/or agent),
o. an antibiotic substance (and/or agent),
p. an antiviral substance (and/or agent), and
q. an antifungal substance (and/or agent).

In further embodiments, at least a portion of the disinfecting portion 304 may be substantially shaped as the following:

a. cylindrical,
b. rectangular,
c. elliptical,
d. curved,
e. pyramidal,
f. box-shaped, and/or
g. any other suitable shape.

In further embodiments, the disinfecting portion 304 may be configured to be removably secured to the core 302 and/or handle portion 200.

In further embodiments, the disinfecting portion 304 may comprise a disinfecting portion cavity 306. The disinfecting portion cavity 306 may be used to receive the core 302 for at least the purpose of securing the core 302 to the disinfecting portion 304. In some embodiments, the disinfecting portion 304 may be configured to envelop, secure to, connect to, and/or fit on the core.

In further embodiments, the disinfecting portion 304 may comprise one or more divots 308. The one or more divots 308 may be used to further secure the disinfecting portion 304 to the handle portion 200. At least a portion of the one or more divots 308 may be configured to receive the one or more flanges 208 of the inner housing 204. At least a portion of the one or more divots 308 may be disposed proximate to a distal end of disinfecting portion 304 housed in the cavity 206 (when the apparatus 100 is in an assembled state).

C. Protective Casing 400

Figure 5:
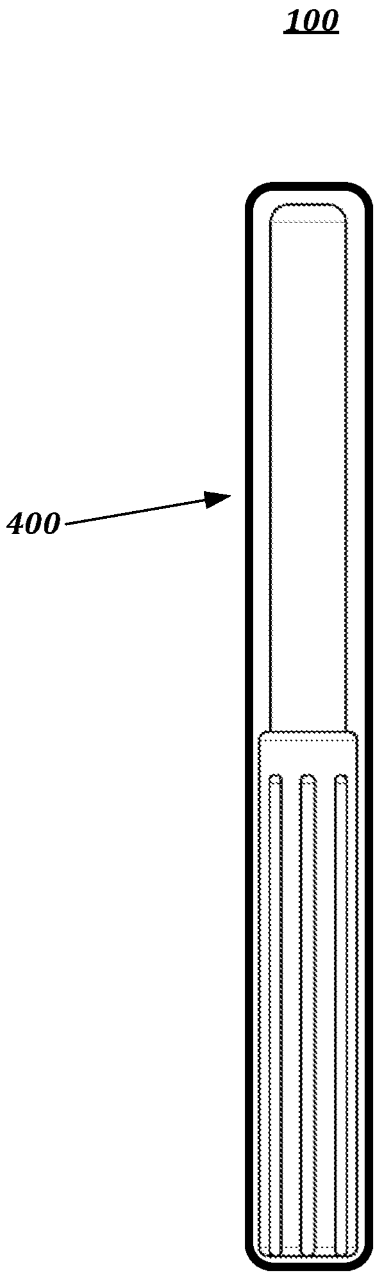
FIG. 5 illustrates a protective casing 400.

At least FIG. 5 illustrates a protective casing 400 consistent with an embodiment of the disclosure may be provided. The protective casing 400 may substantially surround at least the cleaning portion 300 of the sanitizing apparatus 100. In some embodiments, the protective casing 400 may substantially surround the entire sanitizing apparatus 100. The protective casing 400 may be formed such that the sanitizing apparatus 100 may be removed from the protective casing 400. The protective casing 400 may be used to preserve the disinfecting properties of the sanitizing apparatus 100 until use of the sanitizing apparatus 100 is desired. The protective casing 400 may be referred to interchangeably as, but not limited to, a wrapper, a protective layer, a case, and/or an apparatus sealing portion.

In some embodiments, the protective casing 400 may comprise a disposable wrapper. In other embodiments, the protective casing may comprise a reusable casing.

III. APPARATUS/SYSTEM USE

Embodiments of the present disclosure provide a system operative by a set of methods comprising instructions configured to operate the aforementioned components in accordance with the methods. The following depicts an example of a method of a plurality of methods that may be performed by at least one of the aforementioned components. Various hardware components may be used at the various stages of operations disclosed with reference to each component.

For example, although methods may be described to be performed by a single component, it should be understood that, in some embodiments, different operations may be performed by different components in operative relation with one another. For example, the apparatus 100 may be employed in the performance of some or all of the stages disclosed with regard to the methods. As such, the apparatus 100 may comprise at least one architectural component disclosed herein.

Furthermore, although the stages of the following example method are disclosed in a particular order, it should be understood that the order is disclosed for illustrative purposes only. Stages may be combined, separated, reordered, and various intermediary stages may exist. Accordingly, it should be understood that the various stages, in various embodiments, may be performed in arrangements that differ from the ones claimed below. Moreover, various stages may be added or removed from the without altering or deterring from the fundamental scope of the depicted methods and systems disclosed herein.

Consistent with embodiments of the present disclosure, a method 2000 for sanitizing a desired surface may be performed by at least one of the aforementioned components. The method may comprise the following stages:

1. 2002—Providing a sanitizing apparatus housed in a protective case;
2. 2004—Removing the sanitizing apparatus from the protective case;
3. 2006—Securing the sanitizing apparatus to a hand of a user via a handle portion of the sanitizing apparatus; and
4. 2008—Utilizing the handle portion to contact a desired surface with a disinfecting portion of the sanitizing apparatus, thereby sanitizing the contacted portion of the desired surface.

Consistent with embodiments of the present disclosure, a method 3000 for assembling a sanitizing apparatus may be performed by at least one of the aforementioned components. The method may comprise the following stages:

1. 3002—providing a handle portion,
   a. the handle portion comprising:
      i. an internal housing, and
      ii. an external housing;
2. 3004—securing a distal end of a cleaning core to the internal housing of the handle portion,
   a. at least a portion of the cleaning core being made from a rigid material;
3. 3006—securing a cleaning applicator to the cleaning core,
   a. via securing the cleaning core into an aperture or cavity of the cleaning applicator,
   b. at least a portion of the disinfecting portion being housed in the inner housing of the handle portion; and
4. 3008—securing the sanitizing apparatus in a protective casing,
   a. the casing being configured to preserve the disinfecting properties of the sanitizing apparatus until use of the sanitizing apparatus is desired.

Although the stages are disclosed in a particular order, it should be understood that the order is disclosed for illustrative purposes only. Stages may be combined, separated, reordered, and various intermediary stages may exist. Accordingly, it should be understood that the various stages, in various embodiments, may be performed in arrangements that differ from the ones claimed below. Moreover, various stages may be added or removed from the without altering or deterring from the fundamental scope of the depicted methods and systems disclosed herein.

IV. ASPECTS

The following disclose various Aspects of the present disclosure. The various Aspects are not to be construed as patent claims unless the language of the Aspect appears as a patent claim. The Aspects describe various non-limiting embodiments of the present disclosure.

Aspect 1. Application/Use: Push flexible portion against surface and/or toilet seat.

Aspect 2. Sponge/cleaning portion/applicator may retain moisture.

Aspect 3. Apparatus may be pocket sized.

Aspect 4. Apparatus may be one time use.

Aspect 5. Cleaning portion may be interchangeable, reused, and/or recycled.

V. CLAIMS

While the specification includes examples, the disclosure's scope is indicated by the following claims. Furthermore, while the specification has been described in language specific to structural features and/or methodological acts, the claims are not limited to the features or acts described above. Rather, the specific features and acts described above are disclosed as example for embodiments of the disclosure.

Insofar as the description above and the accompanying drawing disclose any additional subject matter that is not within the scope of the claims below, the disclosures are not dedicated to the public and the right to file one or more applications to claims such additional disclosures is reserved.

The following is claimed:

1. A sanitizing apparatus comprising:

a handle portion comprising:

an outer housing configured to be grasped by a hand of a user, an inner housing defining a cavity, the inner housing comprising one or more flanges extending inward from the inner housing, and a rim extending inward from the inner housing, the rim configured to define a predetermined area for housing a portion of a cleaning portion; and the cleaning portion fixedly secured to the handle portion within the predetermined area defined by the rim, the cleaning portion comprising:

a structural core, at least a portion of the structural core being housed in the handle portion, and a pliable disinfecting portion fixed around the structural core, the pliable disinfecting portion comprising one or more divots disposed proximate to an end of the pliable disinfecting portion housed within the handle portion, each of the one or more divots being configured to receive a respective flange of the one or more flanges, wherein at least a portion of the pliable disinfecting portion is disposed in the predetermined area defined by the rim.

2. The apparatus of claim 1, wherein at least a portion of the pliable disinfecting portion is made from a sponge-like material.

3. The apparatus of claim 2, wherein a disinfecting solution is absorbed in the pliable disinfecting portion, the disinfecting solution comprising at least the following:

mugwort, lemongrass, lavender, and orange blossom.

4. The apparatus of claim 3, wherein the disinfecting solution further comprises the following:

benzalkonium chloride, and polyhexamethylene guanidine.

5. The apparatus of claim 1, wherein the outer housing of the handle portion comprises a plurality of grooves, each of the plurality of grooves spanning a longitudinal length of the handle portion, wherein the plurality of grooves is configured to assist with the hand of the user gripping the handle portion.

6. The apparatus of claim 1, wherein each of the one or more divots of the pliable disinfecting portion is sized and shaped to retain the respective flange under a compressive force applied to the pliable disinfecting portion.

7. The apparatus of claim 6, wherein each of the one or more flanges has a cross-sectional profile complementary to a cross-sectional profile of a respective one of the one or more divots.

8. A sanitizing apparatus comprising:

a handle portion;

a disinfecting portion having a substantially cylindrical shape and comprising:

a disinfecting portion aperture, and a plurality of divots disposed proximate to an end of the disinfecting portion, each of the plurality of divots being configured to receive a flange, of a plurality of flanges, within the handle portion; and a disinfecting base housed in the disinfecting portion aperture and protruding from the disinfecting portion, a protruding portion of the disinfecting base being secured within the handle portion.

9. The apparatus of claim 8, wherein a portion of the disinfecting portion is housed within the handle portion.

10. The apparatus of claim 8, wherein the disinfecting base is configured to provide structural integrity to the disinfecting portion.

11. The apparatus of claim 8, wherein the disinfecting portion is made from a substantially porous material.

12. The apparatus of claim 11, wherein a disinfecting solution is absorbed in the substantially porous material, the disinfecting solution comprising at least the following:

mugwort, lemongrass, lavender, and orange blossom.

13. The apparatus of claim 12, wherein the sanitizing apparatus further comprises a protective casing enveloping the sanitizing apparatus.

14. The apparatus of claim 13, wherein the protective casing is configured to preserve disinfecting properties of the sanitizing apparatus until use of the sanitizing apparatus is desired.

15. A sanitizing apparatus comprising:

a handle portion comprising:

an outer housing, and an inner housing defining an aperture;

a core secured to the inner housing by the aperture receiving the core, wherein at least a portion of the core protrudes from the handle portion; and a cleaning applicator secured to the protruding portion of the core, at least a portion of the cleaning applicator being housed in the aperture and secured within the aperture via one or more flanges inserted into one or more divots defined in the cleaning applicator.

16. The apparatus of claim 15, wherein the core provides structural integrity to the cleaning applicator.

17. The apparatus of claim 8, wherein the disinfecting portion is made from a substantially pliable material.

18. The apparatus of claim 17, wherein a disinfecting solution is absorbed in the substantially pliable material, the disinfecting solution comprising at least the following:

water, mugwort, lemongrass, lavender, orange blossom, benzalkonium chloride, and polyhexamethylene guanidine.

19. The apparatus of claim 18, wherein the handle portion comprises an outer housing, the outer housing comprising a plurality of grooves, each of the plurality of grooves spanning a longitudinal length of the handle portion, wherein the plurality of grooves is configured to assist with a hand of a user gripping the handle portion.

20. The apparatus of claim 15, wherein a disinfecting solution is absorbed in the cleaning applicator, the disinfecting solution comprising at least the following:

mugwort, lemongrass, lavender, and orange blossom.

* * * * *